United States Patent [19]

Groves et al.

[11] 4,171,164

[45] Oct. 16, 1979

[54] CONTINUOUS X-RAY ANALYSIS FOR MEAT BLENDING SYSTEM

[75] Inventors: William H. Groves; Andrew E. Donovan, both of Waltham, Mass.

[73] Assignee: The Kartridg Pak Co., Davenport, Iowa

[21] Appl. No.: 859,579

[22] Filed: Dec. 12, 1977

[51] Int. Cl.² ............................................. B01F 15/04
[52] U.S. Cl. .................................... 366/152; 99/486; 250/358 R; 426/231; 426/388
[58] Field of Search ................. 366/152, 160, 161, 17; 99/485, 486; 426/231, 388, 250, 646; 250/358

[56] References Cited

U.S. PATENT DOCUMENTS

| | | | |
|---|---|---|---|
| 2,992,332 | 7/1961 | Madigan | 250/358 |
| 3,050,399 | 8/1962 | Kielsmeier | 426/231 |
| 3,495,808 | 2/1970 | Klein | 366/152 |
| 3,794,301 | 2/1974 | Simmonds | 366/152 |
| 3,851,075 | 11/1974 | Wisdom | 426/250 |

Primary Examiner—Robert W. Jenkins
Attorney, Agent, or Firm—Lockwood, Dewey, Alex & Cummings

[57] ABSTRACT

A method and apparatus is provided for formulating meat blends to a desired fat percentage by continuously measuring in a non-destructive manner the percentage of fat in meat streams while they are flowing, and thereafter blending the streams into the desired formulation. Although the meat streams are of non-uniform consistency and density, accurate blending is accomplished by including a sensor that automatically and continuously monitors the meat streams to enable corrections for such non-uniformity. Percentage fat measurements are made by passing a beam of polychromatic X-rays through the streams and measuring both the incident and attenuated beams.

15 Claims, 5 Drawing Figures

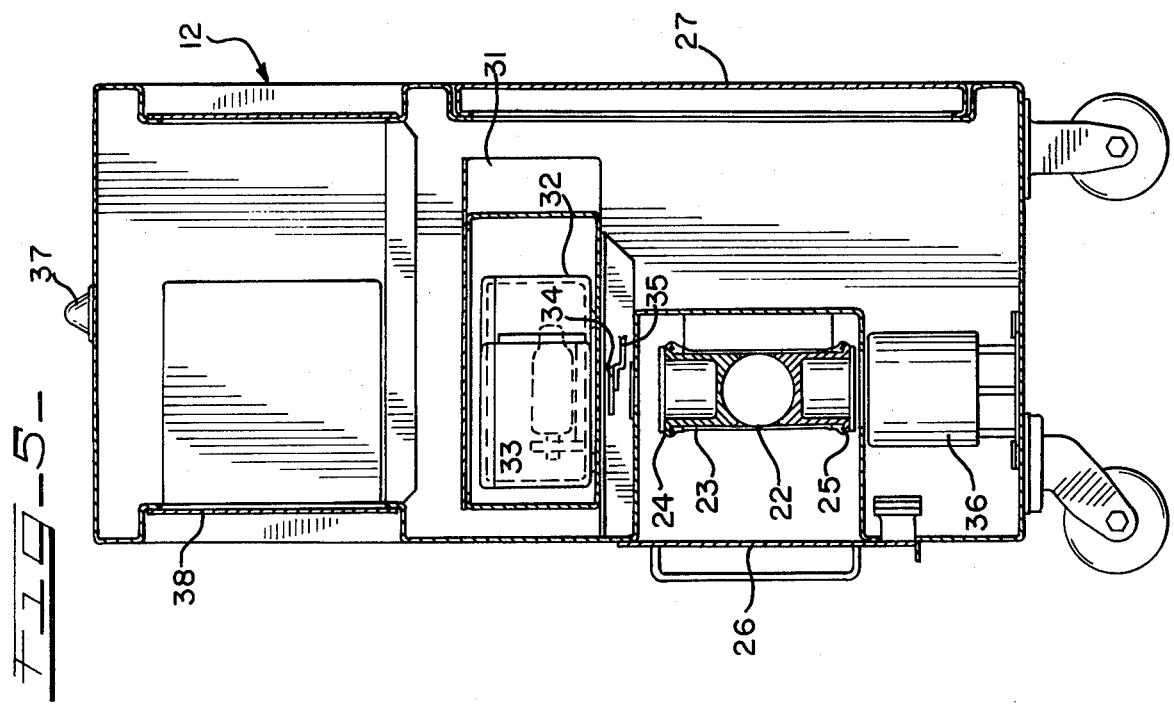
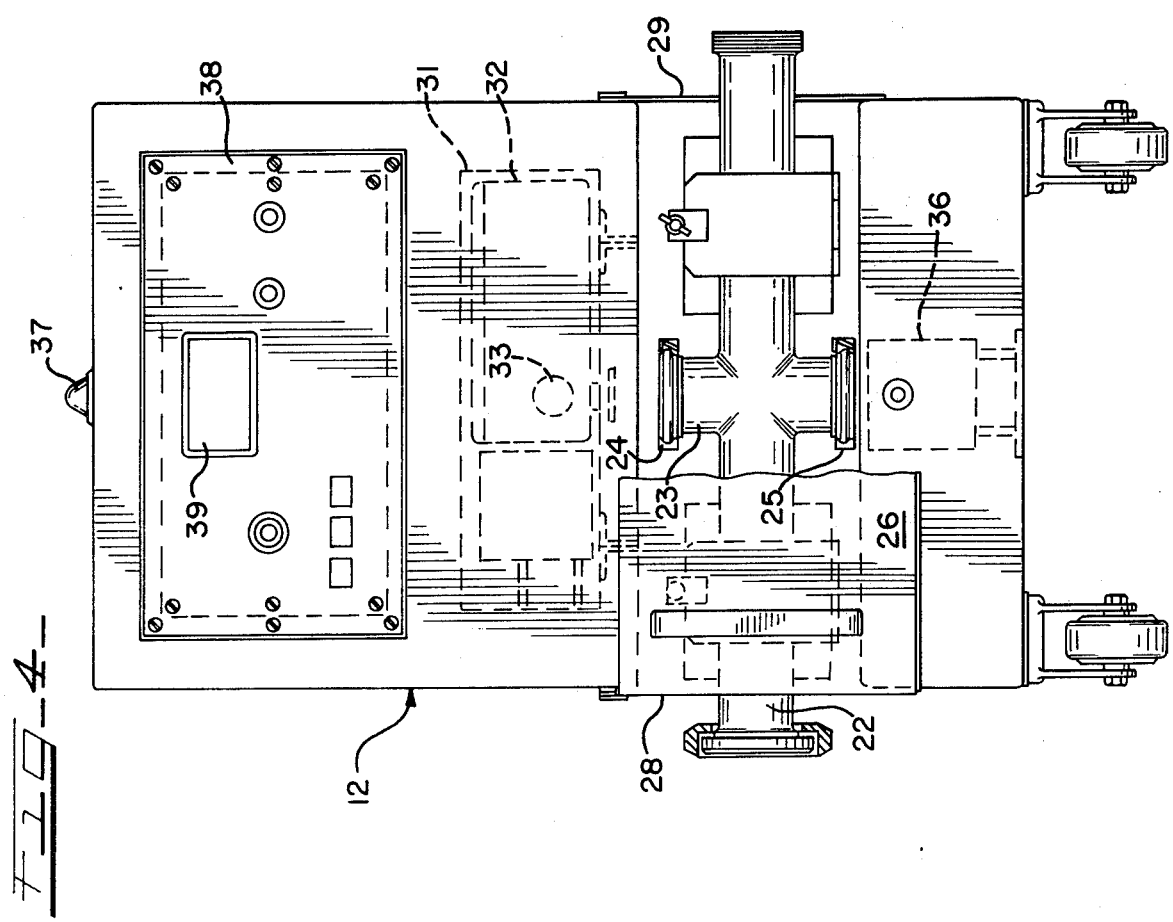

CONTINUOUS X-RAY ANALYSIS FOR MEAT BLENDING SYSTEM

BACKGROUND AND DESCRIPTION OF THE INVENTION

The present invention relates generally to innovations and improvements in meat blending systems incorporating the continuous X-ray analysis of streams of meat and adjusting for the non-uniformity of such streams. It is especially suitable for use in large-scale formulation of sausage and of ground meat.

Using X-ray beams to determine relative amounts of components within materials, such as the quantity of fat within meat, are known, for example, from Madigan U.S. Pat. No. 2,992,332, herein incorporated by reference, which deals with a device for determining the quantitative relationship between meat components by measuring gamma ray penetration thereof. Developments such as these recognize that lean meat has a high concentration of moisture and protein and includes nitrogen and oxygen atoms which are of a greater atomic number than the carbon and hydrogen atoms which predominate in meat fat, meaning that the lean meat absorbs gamma radiation to a far greater extent than does the fat when the gamma rays are within that range of strength wherein the X-ray energy incident upon the meat is attenuated as a result of a phenomenon known as the photoelectric effect. Devices of the type described in Madigan are limited in their usefulness and accuracy because they require periodic offstream statistical sampling of the meat being analyzed, the samples having to be of uniform predetermined weight, size, and geometrical configuration. They also require a high degree of homogeniety of batches tested which is achieved by time-consuming and capital-intensive mixing at each stage.

Copending U.S. Ser. No. 843,702, filed Oct. 19, 1977 by William H. Groves and Andrew E. Donovan, entitled Two-Level X-Ray Analysis for Determining Fat Percentage, recognizes that beam measurements may be conducted at two different energy levels of polychromatic beams, such as the X-rays generated by Coolidge tubes, to analyze meats for fat content even though the meats analyzed have non-uniform weights and sizes so long as they have relatively smooth surfaces. A copending application of Inge B. Henriksen, entitled Multiple-Level X-Ray Analysis for Determining Fat Percentage, eliminates the need to smooth the meat before analysis if it does not already have a relatively smooth surface by using more than two different energy levels of polychromatic beams. Neither copending application deals specifically with the continuous analysis of streams of meat and adjusting for the non-uniformity of such streams.

Representative of patents describing the blending of meat for the purpose of preparing a meat formulation having a predetermined fat content are Gillespi U.S. Pat. No. 3,851,075; Larsen U.S. Pat. No. 3,734,741; and Kielsmeier, et al. U.S. Pat. No. 3,050,399, but none of these patents indicates that its system has the capability of the present invention of using X-ray beams for continuously analyzing entire flowing meat streams of non-uniform consistency in situ while conducting actual measurements on the meat streams in order to account for the non-uniformity thereof so as to enhance the accuracy of the analysis and the invariability of the blended formulation.

A modification of the device as described in said Madigan U.S. Pat. No. 2,992,332 is known by the trade designation of Model M-401 Continuous Anyl-Ray Meat Analyzer. This Model M-401 is a commercially available component of the present invention which is described in more detail herein. A main objective of the Model M-401 itself is to determine, continuously, the percent fat of a meat pumped through it. Basically, it refines the concepts of the Madigan patent so they can be applied to a flow of meat, rather than to only off-stream samples thereof. For accurate analysis results, the meat must be passing therethrough at a constant rate of flow and be free of voids. This device relies on an assemption that it is continuously measuring a uniform sample of a meat flow, although under actual plant conditions such uniformity is not always easily and efficiently attained.

It is accordingly a general object of the present invention to provide an improved means for continuously determining the fat percentages of streams of meat.

Another object of the present invention is an improved method and apparatus using polychromatic X-ray beams and a sensor to monitor the fat content of streams of meat in a manner that accounts for non-uniformities in the streams.

Another object of this invention is an improved method and apparatus for continuously determining the fat content of streams of meat having variable or non-uniform properties, continuously calculating the amounts of such streams that must be added to arrive at a formulation having a desired weight and a desired percent fat, and automatically blending the streams in the proportions needed to achieve the desired formulation.

Another object of this invention is an improved method and apparatus for accurately, automatically and continuously producing meat blends suitable for forming into meat patties of uniform fat percentages.

Another object of the present invention is an improved method and apparatus for automatically preparing meat batches having a desired weight as well as a desired fat percentage for blending with other weighed sausage ingredients during the continuous preparation of sausage formulations.

Another object of the present invention is an improved method and apparatus for producing meat blends of predetermined fat percentage, either in batches of predetermined weight for sausage formulations and the like or in batches of variable weight for ground meat formulations and the like, which can be operated by relatively unskilled labor and under plant operation conditions.

These and other objects of the present invention will be apparent from the following detailed description, taken in conjunction with the accompanying drawings wherein:

FIG. 4 is a detailed side elevational view, partially cut away, of the X-ray analysis unit of FIG. 2; and FIG. 5 is an end elevational view of FIG. 4.

Figure 1:
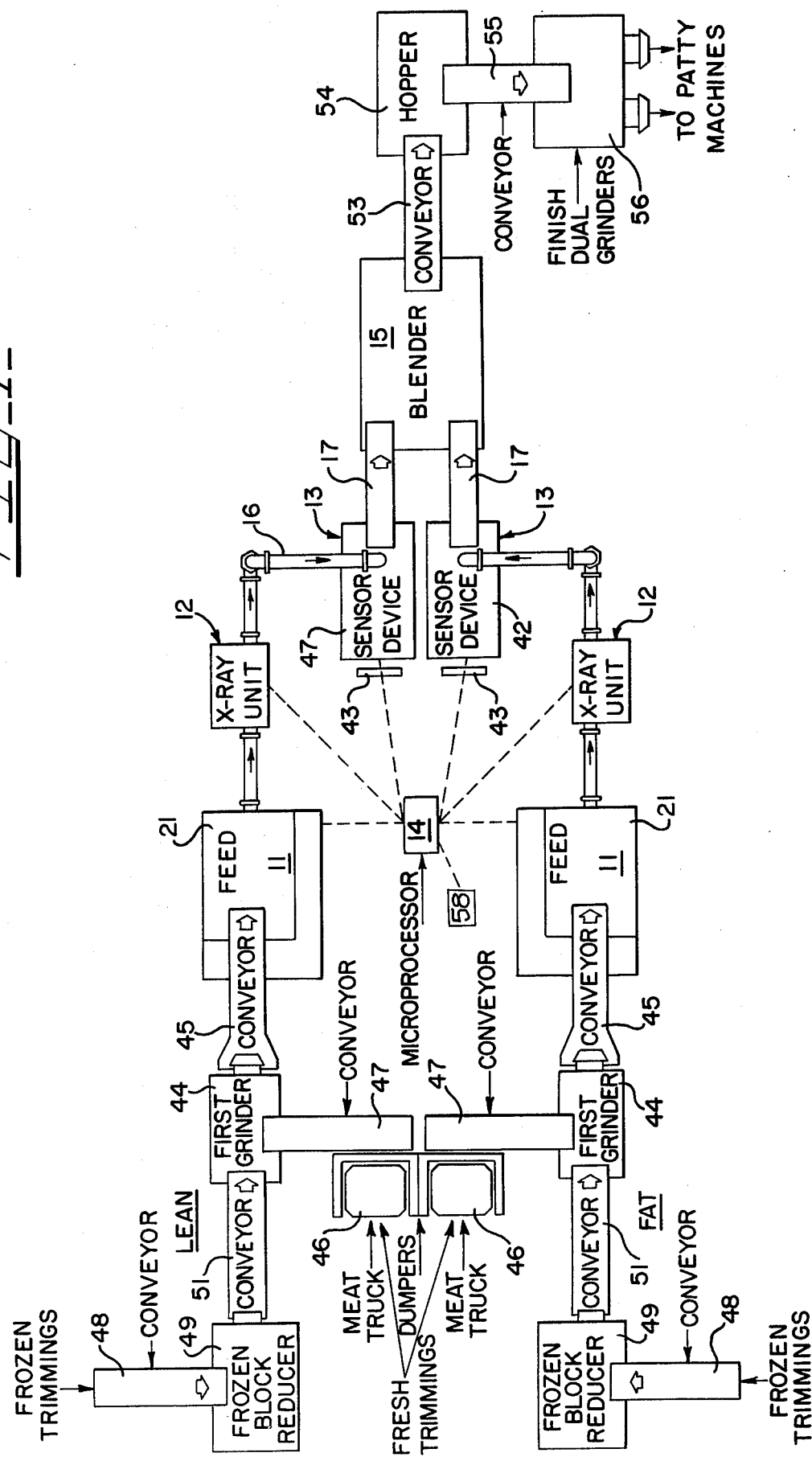
FIG. 1 is a schematic illustration of the preferred apparatus of the present invention, including certain optional features.

The preferred apparatus illustrated schematically in FIG. 1 includes one or more feed means, generally designed by 11, one or more continuous X-ray analysis units, indicated generally by 12, one or more sensor devices, depicted generally as 13, a microprocessor 14, and a blender 15, in communication with each other through suitable conventional conduits 16 and conveyors 17 and/or electrical interconnections where appropriate. Basically, the apparatus provides one meat stream of "lean" meat which has a relatively low fat content, and another meat stream of "fat" meat which has a relatively high fat content, the streams being automatically and continuously analyzed to determine the fat percentage and amount of meat in the streams themselves before they flow into the blender 15 whereby the flows are automatically regulated to form a blended product having a desired fat percentage between those of the "lean" stream and of the "fat" stream.

Figure 2:
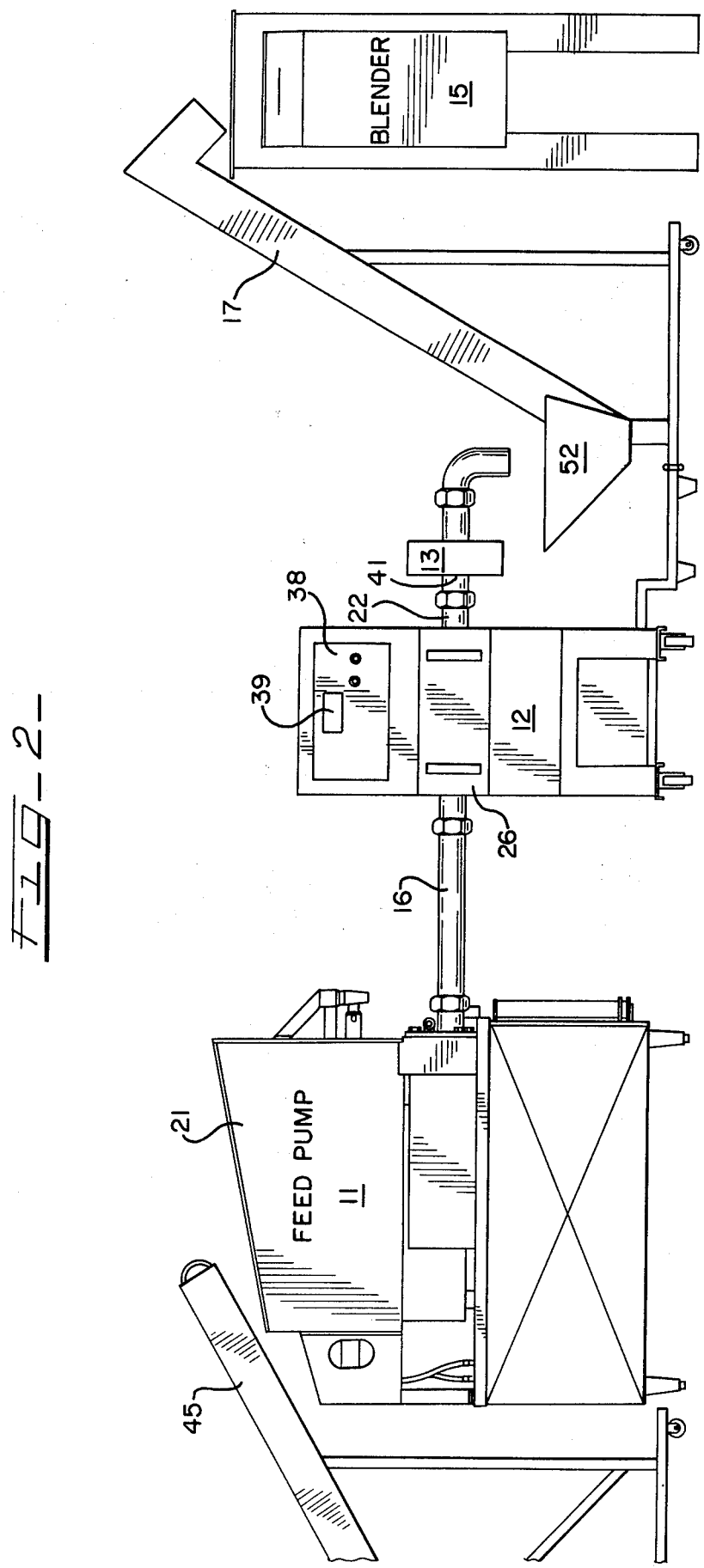
FIG. 2 is a side elevational view of the features illustrated in FIG. 1 from the feed pump and its feed conveyor through the mixer and its feed conveyor.
Figure 3:
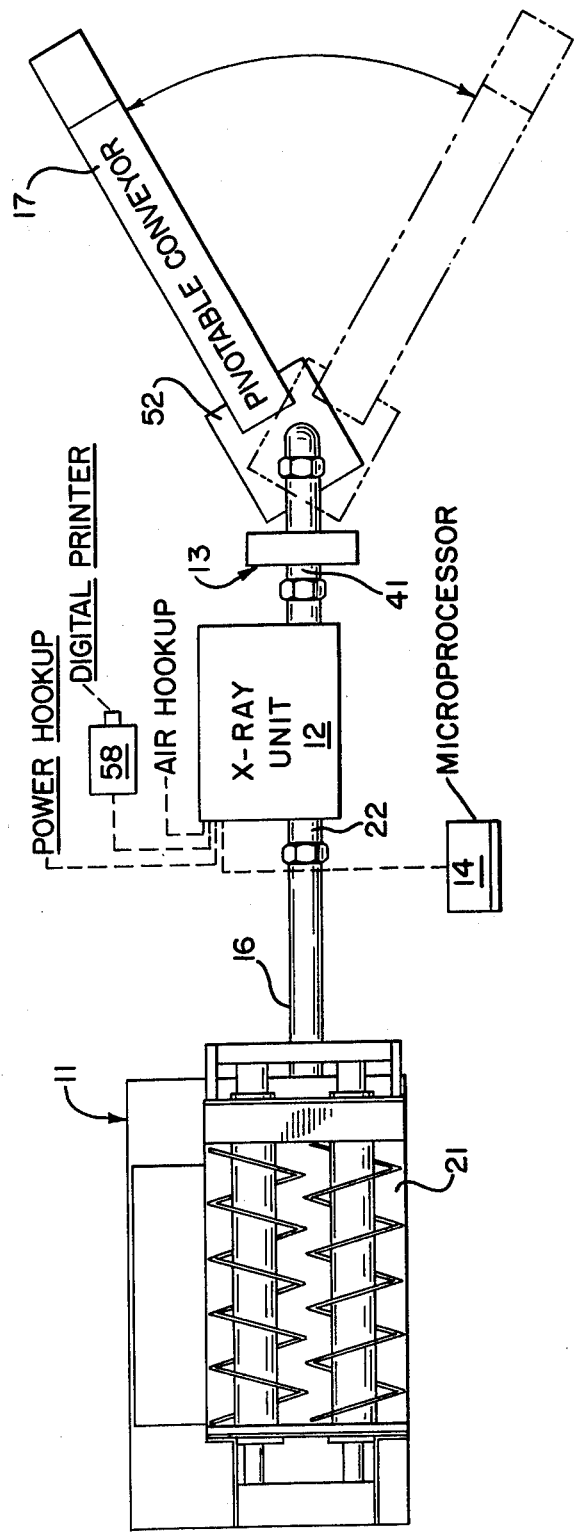
FIG. 3 is a top plan view of the features that are shown in FIG. 2.

Feed means 11 includes a hopper 21 for storing meat before it is passed on by the means 11 to the rest of the system. For most accurate final blending, feed means 11 should supply the meat stream with generally consistent compaction and at a generally constant flow rate in order to reduce the magnitude of the corrections being made from the output of the sensor device 13, thereby increasing the accuracy of the corrections. A device such as a gear pump of known construction is adequate in this regard for soft meat streams, such as hot pork, but introduces a relatively large error factor when pumping colder meats because such colder meats are more difficult to pump making them resistant to being formed into a well-compacted stream moving at a relatively uniform velocity. The preferred feed means 11, shown in FIGS. 2 and 3, is a pump known in the art as a Model 313-1 Stuffing Pump (The Kartridg Pak Co.) having a 1,000-pound capacity hopper 21. Such a pump is particularly well suited for moving meat since it pulls a vacuum to reduce air voids between the meat as it is being pumped, thereby enhancing the consistency of the pumped flow. Alternatively, under some circumstances, feed means 11 need not include a pump as such. A grinder of the type commonly used in the trade may with suitable adaptations be used to provide the pumping action required by the system.

X-ray analysis unit 12 incorporates radiation to determine the fat percentage of a moving meat stream as it passes through a pipe of known size. The preferred unit 12 is an Anyl-Ray Model M-401 (Anyl-Ray Corporation) shown in FIGS. 4 and 5. Meat enters unit 12 through a pipe cross 22 having a vertical leg 23 with top and bottom windows 24, 25, permitting the passage of radiation therethrough. Access to the pipe cross 22 is gained through a sliding door 26, partially broken away in FIG. 4, a rear access panel 27, and end plates 28, 29, one of which has been removed in FIG. 5.

Included within a housing 31 and a casting 32 of aluminum filled with high dielectric silicon oil is an X-ray tube 33. The X-rays pass through aperture 34 having a failsafe shutter 35 which is interlocked with the feed pump 11 and which automatically closes when the feed means 11 stops in order to prevent continuous X-ray exposure while the stream has stopped. Ionization chamber 36 monitors the attenuated X-ray beams after they have passed through top window 24, the portion of the meat streams within the pipe cross 22, and the bottom window 25. An indicator light 37 warns that the X-ray device is turned on. A control panel 38 includes a percentage fat read-out display 39.

Sensor device 13 monitors the meat stream after it has passed through the X-ray unit 12 and generates data useful in increasing the accuracy of the total system by being able to record how much meat has been pumped through the X-ray unit 12. Without such a sensor device 13, it is necessary to estimate the velocity or rate of flow of the stream and calculate the amount of meat, usually as a function of elapsed time. Device 13 can take the form of a means for measuring the velocity by monitoring the meat particles as they flow, for example, from the X-ray unit 12 at 41 in FIGS. 2 and 3. Or, in its preferred form and as illustrated in FIG. 1, device 13 can be a so-called load cell (National Controls) of known construction, being, in essence a collection hopper 42, that is also an electronic scale having electrical strain gauges to provide weight data in digital form, which can be displayed at 43.

Preferably, when the meat temperature is below 50° F., the conduits 16 and pipe cross 52 are jacketed and water heated to promote flow of meat therethrough by preventing the buildup of meat on the interior of the conduits 16. Conventional jacketed piping can be used for this purpose.

Microprocessor 14 receives data from or controls the feed means 11, the X-ray unit 12, and the sensor device 13. A primary operation of the microprocessor 14 is to receive the percentage fat data and the weight data and from these to regulate the operation of the feed means 11 for ultimately arriving at the desired fat percentage blend and, if also desired, the total formulation batch weight. A typical acceptable microprocessor 14 uses the Motorola 6800 series sytem. Any large scale office computer, such as an IBM 370 model computer, could be used for this purpose. Most digital computers would be acceptable, preferably having eight-bit or greater capabilities.

Various additional means can be incorporated to provide the fully automated system illustrated in FIG. 1. Two separate feed means 11, X-ray units 12, and sensor devices 13 are used, one of each for the "lean" meat stream and the other of each for the "fat" meat stream. Each feed means 11 is stocked with either or both of frozen and fresh meat by a conveyor system which includes first grinders 44 for passing the meat through a grinding head of between ⅜ inch to ¾ inch in size. Feed conveyors 45 pass this ground meat into the hoppers 21 of the feed pumps 11. Fresh meat is simply loaded from meat trucks onto dumpers 46, and from there it is passed by conveyors 47 to the grinders 44. Frozen trimmings are preferably loaded onto conveyors 48 for transport to frozen block reducers 49 to break up the large frozen blocks, after which the conveyors 51 introduce the frozen meat supply into the grinders 44.

Conveyors 17 transport the analyzed meat streams from the hoppers 42 of the sensor devices 13 of from collection troughs 52 (FIG. 2) down-line of the sensor devices 13. The combined formulations leave blender 15 by means of a conveyor 53 for storage in a hopper 54, after which the formulations can be further conveyed by means 55 into dual finish grinders 56 when the formulations are to be used in patty-making machines. For additional flexibility, the conveyor 17 may be pivotable (FIGS. 2 and 3).

A digital printer station 58 can be associated with the system at a control location remote from the apparatus itself, typically displaying the following information;

percent fat of the "lean" stream, weight of the "lean" material having passed through that stream, percent fat of the "fat" stream, weight of the "fat" material having passed through that stream, percent fat of the blend, total weight of the blend, the time of day, and the batch number. Station 58 may include other useful instruments such as manual controls for the X-ray units 12.

The method according to the present invention proceeds with continuous analysis and monitoring of substantially entire streams of meat combined into a meat blend having a desired fat percentage. It includes supplying meat in the form of a stream, continuously analyzing the stream for fat content as it flows past a particular location, continuously monitoring the stream for measuring the amount of meat analyzed, supplying another meat stream, analyzing and monitoring it in substantially the same manner, and automatically blending the two streams in proportions for arriving at a meat having a desired fat percentage.

When preparing a blend of a desired fat percentage as a batch of an unspecified total weight, e.g. when preparing a desired variety of ground meat, the steps may be carried out in serial fashion whereby an analyzed and monitored batch of one stream of meat is passed and stored, and then another stream is analyzed continuously and monitored until enough of this other stream passes to the storage location so that, when blended with the previously batched stream, the desired fat percentage will be arrived at. When preparing a blend of a desired fat percentage that is also of a given total weight, useful when formulating a sausage recipe so that predetermined quantities of other ingredients such as spices may be readily added to the blended meat, the steps are carried out in a simultaneous fashion whereby two streams are analyzed and monitored continuously and generally simultaneously with each other, the flow of each stream being regulated in accordance with calculations of current and projected blend fat percentage and blend weight.

When proceeding in accordance with either aspect of the present method, the serial concept or the simultaneous operation concept, the object achieved is that of formulating large quantities of meat blends to a desired fat percentage. For example, the simultaneous operation concept as illustrated in FIG. 1 produces either a sausage recipe or predetermined amounts of ground meat at a desired fat percentage at rates as fast as 500 pounds per minute.

Referring to the method in more detail, the preferred meat stream supplying step includes pumping a stream of ground meat through closed conduits from which some entrapped air pockets have been removed by drawing a vacuum on the ground meat as it is pumped. Such a pumping step will reduce changes in the rate of flow and eliminate errors in the X-ray analysis due to the presence of air pockets in the meat stream. Uniformity of flow can also be improved by heating the conduits through which the meat is pumped to reduce fat build-up therewithin. Prior to the pumping step, a grinding step can provide fresh and/or frozen meat in a roughly ground form, usually between about ⅜ inch to ¾ inch in size, to increase the pumpability thereof. In some cases, an alternative meat stream supplying step can be practiced by omitting the pumping step whereby the analyzing step follows directly after the grinding step. This requires a grinder capable of producing a continuous flow having substantially no air pockets.

In the analyzing step, the fat percentage of the meat as it passes a particular location in the stream is determined by X-ray beam attenuation generally in a manner as described in said Madigan U.S. Pat. No. 2,992,332. Beams of polychromatic X-ray radiation are passed through the meat stream, the beams being attenuated thereby, and the degree of attenuation being used to calculate fat percentages in accordance with known procedures, usually using attenuations of calibration standards corresponding to fat percentage values. The fat percentage at the beginning of any cycle is thereafter continuously integrated with subsequent fat percentage readings to obtain a continuously updated value for the fat percentage of the total quantity of meat analyzed since the beginning of the cycle.

The monitoring step uses a sensor means to determine the amount of meat that has flowed during the analyzing step in arriving at the integrated fat percentage value. Such monitoring step can include weighing the meat previously analyzed. It can include, alternatively, measuring the velocity of the meat stream to calculate the amount of meat thereby. Data accumulated in the monitoring step is incorporated with the fat percentage data, each with respect to both meat streams, into ratio relationships to calculate and project blended fat percentages and, if desired, blend weights. Monitoring step data can also be used to correct the analyzing step data for errors arising during that step from assumptions inherent in the analyzing step per se to the effect that the flow is at a constant rate of weight per unit time and that air voids have been removed from the stream. Such errors arise in the analyzing step since said step recognizes X-ray beam attenuation brought about by air pockets and since the basic techniques thereof are founded on analyzing a given weight of meat flowing past the analysis location within the stream.

In the blending step, the streams are combined by conventional mixing techniques into the desired formulation. The microprocessor uses data generated in the analyzing and monitoring steps to automatically and quickly set up and determine the ratios between fat percentages and amounts of meat and then uses these data to regulate the rate of the supplying step for one or both of the streams and to make corrections in the analyzing step data. Ratio calculations are facilitated by providing meat streams having significantly different integrated fat percentages so they can be classified as a "lean" meat stream, fat content on the order of 10 to 20 percent fat, and a "fat" meat stream, fat content on the order of 50 to 60 percent fat. The target fat percent of the blend will be between such "lean" and "fat" values.

The following examples more precisely illustrate the invention and teach the procedures presently preferred for practicing the same.

EXAMPLE I

The hoppers of two Model 313-1 Stuffing Pumps (The Kartridg Pak Co.) are fed with meat ground to between about ⅜ inch and ¾ inch in size, one pump being fed with "lean" pork or beef, the other being fed with "high fat" pork or beef. The discharge end of each pump is fitted with 4 inch outside diameter piping running to the inlet end of the pipe cross of a calibrated Model M-401 Continuous Anyl-Ray (Anyl-Ray Corporation), and the outlet end of each pipe cross is fitted wih 4 inch outside diameter piping to contain the meat streams and to direct the streams to the collection hopper one of two load cells (National Controls). Each load cell measures the weight of the meat stream analyzed by each Anyl-Ray before it passes to a conventional meat blender, and all data is fed to a microprocessor incorporating a Motorola Series 6800 digital computer system at an operator's control panel remote from the blending line itself. The feed pump on the "lean" line is set to run at about maximum speed (500 pounds per minute), and the other feed pump is run at a speed that will maintain the projected blended fat percentage below the target fat percentage, which speed relationships are determined by using the ratios incorporated into the following blending equation:

(H%) (H wt.)+(L%) (L wt.)=(B%) (H wt.+L wt.)

where H% is the instantaneous, integrated fat percentage reading of the Anyl-Ray on the "high fat" stream, one such reading being 54.3%; H wt. is the accumulated weight reading of the load cell on the "high fat" stream; L% is the instantaneous, integrated fat percentage reading of the Anyl-Ray on the "lean" stream, one such reading being 12.3%; L wt. is the accumulated weight reading of the load cell on the "lean" stream; and B% is the desired or target fat percentage of the blended meat, in this instance 19.0%.

In this example, since a desired blend total weight is targeted, the microprocessor continuously solves the blending equation by simultaneously considering data from both streams and stops the "lean" feed pump at the time when both (B%) and (H wt.+L wt.) will reach their target values simultaneously with only the "high fat" feed pump running at the end of the cycle. Both collection hoppers of the load cells are emptied into the blender, together with other sausage ingredients such as salt and spices, mixed therein, and then fed to conventional sausage processing equipment. Meanwhile, another cycle has begun to again fill the load cell collection hoppers.

EXAMPLE II

Apparatus as described in Example I is used except only a single line is set up, and the "high fat" stream and the "lean" stream are run on the same equipment, one after the other, so as to achieve a target fat percentage blend of unspecified total weight. First, the "lean" meat is fed through the line and collected in the blender bin, the total weight and the integrated fat percentage thereof being entered in the microprocessor. Then the "high fat" meat is fed though the line and into the bin. As the integrated fat percentage of the "high fat" stream is developed, the microprocessor calculates the weight of this stream that has to be added to achieve the target fat percentage and automatically stops the feed pump and thus the "high fat" stream when the target is reached.

It will be apparent to those skilled in this art that the present invention can be embodied in various forms; accordingly, this invention is to be construed and limited only by the scope of the appended claims.

We claim:
1. An apparatus for automatically blending meat to a desired fat percentage, comprising:
   feed means for producing a continuous stream of meat;
   a fat analysis unit down-line of said feed means for continuously determining the ongoing fat percentage of said stream of meat;
   a sensor device for monitoring the meat stream through said fat analysis unit to measure how much meat passes therethrough;
   a microprocessor for receiving data from said fat analysis unit and from said sensor device, said microprocessor utilizing said data to regulate said feed means; and
   meat blender means down-line of said feed means, said fat analysis unit and said sensor device for mixing meat that has passed therethrough.
2. The apparatus of claim 1, wherein said feed means is a meat pumping unit which pulls a vacuum as it pumps in order to reduce air voids in the pumped meat.
3. The apparatus of claim 1, wherein said feed means is a gear pump.
4. The apparatus of claim 1, wherein said feed means is a meat grinder.
5. The apparatus of claim 1, wherein said fat analysis unit includes a pipe cross through which the meat stream flows, an X-ray tube for transmitting radiation beams through said pipe cross, and an ionization chamber for monitoring attenuated X-ray beams that passed passes through said pipe cross.
6. The apparatus of claim 5, wherein said pipe cross of said fat analysis unit includes a vertical leg having a top and a bottom window to permit substantially unattenuated passage of radiation beams therethrough, and wherein a shutter is positioned between said X-ray tube and said vertical leg, said shutter closing automatically when said feed means stops.
7. The apparatus of claim 1, wherein said sensor device is a load cell including a collection hopper having an electronic scale for weighing the meat stream accumulated within said collection hopper.
8. The apparatus of claim 1, wherein said sensor device is a means for measuring the velocity of the flowing meat stream.
9. The apparatus of claim 1, wherein said fat analysis unit and said sensor device communicate with each other through heated conduit.
10. The apparatus of claim 1, wherein said feed means and said fat analysis unit communicate with each other through heated conduit.
11. The apparatus of claim 1, wherein said microprocessor is a digital computer means.
12. The apparatus of claim 1, further comprising dual lines, both including one said feed means, said fat analysis unit and said sensor device, each said line being up-line of said meat blending means.
13. The apparatus of claim 1, further including reducing means and grinding means up-line of said feed means for enhancing the pumpability of fresh and frozen meat.
14. An apparatus for automatically blending meat to a desired fat percentage, comprising:
   a meat feeding means capable of producing a generally continuous flow substantially free of air pockets;
   a continuous fat analysis unit down-line of said meat feeding means, said fat analysis unit including a pipe cross for receiving meat streams from said meat feeding means, an X-ray tube for transmitting radiation beams through said pipe cross, and an ionization chamber for monitoring attenuated X-ray beams that have passed through said pipe cross;
   a load cell for monitoring meat passing through said continuous fat analysis unit, said load cell including a collection hopper having electronic weighing means;

a microprocessor having digital computer means for receiving data from said continuous fat analysis unit and from said load cell, said microprocessor utilizing said data to regulate said meat feeding means; and meat blender means for mixing meat that has passed through said meat feeding means, said continuous fat analysis unit and said load cell.

15. The apparatus of claim 14, further comprising dual lines, both including one said meat feeding means, said continuous fat analysis unit and said load cell, both of said lines opening into a single one of said meat blender means.

* * * * *